(12) United States Patent
Tann et al.

(10) Patent No.: US 8,859,464 B2
(45) Date of Patent: *Oct. 14, 2014

(54) NITROGEN CONTAINING ISETHIONIC ACID SALTS IN FIELD READY SPRAY AND TANK MIXES

(75) Inventors: R. Scott Tann, Sugar Land, TX (US); Howard M. Stridde, Shiner, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/264,465

(22) PCT Filed: Apr. 23, 2010

(86) PCT No.: PCT/US2010/032146
§ 371 (c)(1),
(2), (4) Date: Oct. 14, 2011

(87) PCT Pub. No.: WO2010/124151
PCT Pub. Date: Oct. 28, 2010

(65) Prior Publication Data
US 2012/0040831 A1  Feb. 16, 2012

Related U.S. Application Data

(60) Provisional application No. 61/172,398, filed on Apr. 24, 2009.

(51) Int. Cl.
| | | |
|---|---|---|
| A01N 57/20 | (2006.01) | |
| A01N 57/10 | (2006.01) | |
| A01N 47/08 | (2006.01) | |
| A01P 21/00 | (2006.01) | |
| A01P 3/00 | (2006.01) | |
| A01P 5/00 | (2006.01) | |
| A01P 9/00 | (2006.01) | |
| A01P 11/00 | (2006.01) | |
| A01P 15/00 | (2006.01) | |

(52) U.S. Cl.
CPC ............................... *A01N 57/20* (2013.01)
USPC ........... 504/127; 504/148; 514/665; 514/642; 514/114

(58) Field of Classification Search
None
See application file for complete search history.

(56) References Cited

U.S. PATENT DOCUMENTS

| | | | |
|---|---|---|---|
| 2,913,324 A | 11/1959 | Kosmin | |
| 3,951,842 A | 4/1976 | Prince et al. | |
| 4,571,309 A * | 2/1986 | Lege | 560/127 |
| 5,352,822 A * | 10/1994 | Blade et al. | 562/492 |
| 5,646,320 A * | 7/1997 | Cassady et al. | 554/149 |
| 6,117,816 A | 9/2000 | Jimoh et al. | |
| 6,455,473 B2 * | 9/2002 | Wright | 504/206 |
| 6,746,988 B2 * | 6/2004 | Hopkinson et al. | 504/127 |
| 2007/0037708 A1 * | 2/2007 | Prosch et al. | 504/206 |

FOREIGN PATENT DOCUMENTS

WO   WO 2010/009820 A   1/2010

OTHER PUBLICATIONS

"Ammonium Cocoyl Isethionate", EWG's Skin Deep Cosmetics Database, <http://www.ewg.org/skindeep/ingredient/716631/AMMONIUM_COCOYL_ISETHIONATE/>, copyright 2007-2012, p. 1.*
Gillco Ingredients, "Food Emulsifiers", <http://www.gillco.com/pr_emulsifiers.php>, Sep. 26, 2008. p. 1.*
antiagingchoices.com, "Sodium Lauryl Sulfate (SLS) in your Personal Care Products", <http://antiagingchoices.com/harmful_ingredients/sodium_lauryl_sulfate.htm>, Copyright 1999-2009, Revised Feb. 13, 2012, p. 1.*
World Health Organization, "Glyphosate and AMPA in Drinking-water: Background document for development of WHO Guidelines for Drinking-water Quality", copyright World Health Organization 2005, pp. 9.*
Kumar, L. et al., "Salt Selection in Drug Development", Pharmaceutical Technology, vol. 3, Issue 32, Mar. 2, 2008, pp. 1-18. <http://www.pharmtech.com/pharmtech/Peer-Reviewed+Research/Salt-Selection-in-Drug-Development/ArticleStandard/Article/detail/500407>.*
Pesticide News, "Glyphosate Fact Sheet", <http://www.pan-uk.org/pestnews/Actives/glyphosa.htm>, No. 33, Sep. 1996, p. 1-4.*
Tharp, C., "Water Quality and Pesticide Performance," <http://www.pesticides.montana.edu/present/Water%20Quality%20and%20Pesticide%20Performance%20Handout.pdf>, Feb. 1, 2001, p. 1-4.*

\* cited by examiner

*Primary Examiner* — Tracy Vivlemore
*Assistant Examiner* — Monica Shin
(74) *Attorney, Agent, or Firm* — Huntsman International LLC

(57) ABSTRACT

Embodiments of the present invention disclose an agricultural composition that is a field ready spray or a tank mix that includes at least one nitrogen containing isethionic acid salt, at least one agriculturally active ingredient, and at least one surfactant.

9 Claims, No Drawings

NITROGEN CONTAINING ISETHIONIC ACID SALTS IN FIELD READY SPRAY AND TANK MIXES

CROSS-REFERENCE TO RELATED APPLICATIONS

This application is the National Phase of International Application PCT/US2010/032146 filed Apr. 23, 2010 which designated the U.S. and which claims priority to U.S. Provisional App. Ser. No. 61/172,398 filed Apr. 24, 2009. The noted applications are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates generally to agricultural compositions, in particular to field ready spray and tank mixes that include nitrogen containing isethionic acid salts.

2. Background of the Invention

It is known that multivalent water hardness ions (calcium, magnesium, iron, etc.) can inhibit the efficacy of numerous pesticides, especially weak acid herbicides. For example, the efficacy of glyphosate (N-phosphonomethyl glycine) is compromised when combined in a hard water solution containing calcium and magnesium ions. Calcium and magnesium ions will bind to glyphosate and render it less effective. This phenomenon is typical with aminophosphate herbicides as well as other weak acid herbicides. To overcome this problem, current commercial manufacturers of weak acid herbicide formulations recommend on their label the inclusion of ammonium sulfate in the spray solution. Numerous research studies have shown that ammonium sulfate in the spray tank solution will reduce the effect of the hard water ions on the efficacy of glyphosate formulations.

However, spray solutions that use ammonium sulfate have drawbacks. Ammonium sulfate grades range in color and purity. Often the applicator is force to handle large amounts of bulky un-dissolved solid lumps of ammonium sulfate which have absorbed moisture. These materials are hard to handle and do not dissolve easily in the spray solution. This leads to blocked filter screens in the spray rig and plugged nozzle tips during applications.

One way to overcome this disadvantage is to formulate the ammonium sulfate into a blended tank mix adjuvant formulation. These unfortunately can also have limitations and their own unique issues. Current commercial adjuvant formulations that contain ammonium sulfate have limitations based on the solubility of the ammonium sulfate. The high solids content necessary to achieve the water conditioning effects from the ammonium sulfate may cause incompatibilities in the formulated tank mix adjuvant. Other components in the formulation may have incompatibilities due to the lack of water in the product. Similarly these materials may not be present at proper rates and reduce the overall efficacy of the ammonium sulfate and the adjuvant component. This may have the further disadvantage of preventing the use of some companion herbicides and adjuvants in the spray tank.

The use of ammonium sulfate may limit the efficacy of the pesticide on the vegetation. The ammonium sulfate formulation may reduce the surface properties of the spray solution in the spray tank and may limit the effectiveness of the pesticide on the target organism.

BRIEF SUMMARY OF SOME OF THE PREFERRED EMBODIMENTS

In a first aspect, embodiments of the present invention disclose an agricultural composition that is a field ready spray or a tank mix that includes at least one nitrogen containing isethionic acid salt, an agriculturally active ingredient, and at least one surfactant.

In an embodiment of the present invention, the at least one nitrogen containing isethionic acid salt has a cationic nitrogen containing group that is an alkyl amine, an alkylalkanolamine or a cyclic amine.

In an embodiment of the present invention, the at least one nitrogen containing isethionic acid salt comprises ammonium isethionic acid salt.

In an embodiment of the present invention, the at least one nitrogen containing isethionic acid salt comprises tallow amine isethionic acid salt.

In an embodiment of the present invention, the at least one nitrogen containing isethionic acid salt comprises a derivative of a nitrogen containing isethionic acid salt.

In an embodiment of the present invention, the derivative of the nitrogen containing isethionic acid salt comprises nitrogen containing isethionic methyl acid salt.

In an embodiment of the present invention, the at least one nitrogen containing isethionic acid salt further comprises isethionic acid.

In an embodiment of the present invention, the agriculturally active ingredient is a weak acid agriculturally active ingredient.

In an embodiment of the present invention, the agriculturally active ingredient is n-phosphonomethylglycine (glyphosate) present in any of its commonly used agriculturally acceptable salts.

In an embodiment of the present invention, the agriculturally active ingredient is selected from the group consisting of: an insecticide, a fungicide, a biocide, a molluscicide, an algaicide, a plant growth regulator, an anthelmintic, a rodenticide, a nematocide, an acaricide, an amoebicide, a protozoacide, a crop safener and a combination thereof.

In an embodiment of the present invention, the at least one surfactant comprises one or more surface active agents capable of reducing the surface tension of water.

In a second aspect of the present invention, a method of treatment of vegetation is disclosed comprising the step of contacting the agricultural composition to vegetation. The agricultural composition is a field ready spray or a tank mix that includes at least one nitrogen containing isethionic acid salt, an agriculturally active ingredient, and at least one surfactant.

In a third aspect, embodiments of the present invention disclose a method of treatment of a substrate comprising the step of contacting the registerable, stable agricultural formulation to the stable registerable formulation to the substrate requiring treatment.

In a fourth aspect, embodiments of the present invention disclose an agricultural adjuvant composition that includes at least one nitrogen containing isethionic acid salt and at least one surfactant.

The foregoing has outlined rather broadly the features of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other compositions for carrying out the same purposes of the present invention. It should also be realized by those skilled in the art that such equivalent compositions do not depart from the spirit and scope of the invention as set forth in the appended claims.

DETAILED DESCRIPTION OF THE PREFERRED EMBODIMENTS

In embodiments of the present invention, it has now been surprisingly found that of field ready sprays and tank mixes containing weak acid herbicides and nitrogen containing isethionic acid salts typically have unique water conditioning characteristics and enhanced biological efficacy.

Embodiments of the present invention disclose an agricultural composition that includes at least one nitrogen containing isethionic acid salt, an agriculturally active ingredient, and at least one surfactant. The agricultural composition is a field ready spray or a tank mix.

Embodiments of the present invention include at least one nitrogen containing isethionic acid salt. The nitrogen containing species of the salt may be any cationic nitrogen containing group. Examples of cationic nitrogen containing groups may be alkyl amines, alkoxylated alkylamines and cyclic amines. Specific examples of the nitrogen containing group may include ammonium, alkyl amines and their ethoxylated derivatives, fatty amines (e.g. tallow amine, coco amine and soya amines) and their ethoxylated derivatives, ethyleneamines, ethanolamines, morpholines, substituted propylamines, polyol amines (such as JEFFAMINE® amines as available from Huntsman Corporation of The Woodlands, Tex.), N-alkylalkyldiamines and their alkoxylated derivatives, N,N-alkyldiamines and their alkoxylated derivatives and combinations thereof. One skilled in the art will recognize appropriate nitrogen containing cationic species to use in embodiments of the present invention.

The anionic part of the salt includes isethionic acid. Isethionic acid has the general formula $HSO_3—CH_2—CH_2—OH$. Two versions of isethionic acid, the second being a derivative of the first (isethionic methyl acid), may be produced using the following reactions:

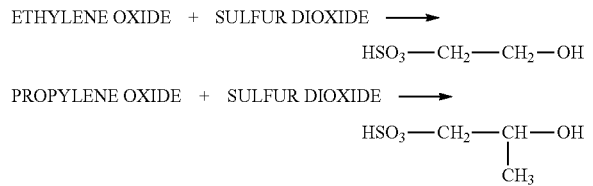

The isethionic acid is neutralized to form the salt. The isethionic acid may be neutralized, separately or in combination, with such reactants as ammonia, and other nitrogen containing groups listed above and/or tallow amine ethoxylates. For example, a tallow amine ethoxylate would form the following salt with isethionic acid:

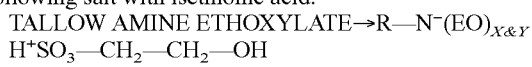

The nitrogen containing isethionic acid salt may further include isethionic acid (non-nueutralized species). In another embodiment, the nitrogen containing isethionic acid salt comprises a derivatives of nitrogen containing isethionic acid salts. An example of a derivative of a nitrogen containing isethionic acid salt would be nitrogen containing isethionic methyl acid salt (whose non-neutralized acid is featured above). One skilled in the art, with the benefit of this disclosure, will recognize appropriate nitrogen containing isethionic acid salts for use in the present invention.

Embodiments of the present invention include at least one agriculturally active ingredient. The agriculturally active ingredients may include water soluble herbicides, fertilizers and combinations thereof, including without limitation, aminophosphate herbicides. In an embodiment, the agriculturally active ingredient is a weak acid herbicide. Weak acid herbicides may include without limitation, glyphosate, glufosinate, bipyridylquaternary ammonium salts (bipyridinium salt) such as paraquat and diquat, salts of phenoxy acids such as 2,4-dichlorophenoxyacetic acid, meta-chlorophenoxyacetic acid (MCPA), picloram, triclopyr and fluroxypyr, and bromoxynil.

As used herein, "glyphosate" means N-phosphonomethylglycine in its acid form or any agriculturally acceptable salt thereof as well as any composition or formulation containing a glyphosate herbicide. "Glyphosate herbicide" means any form of glyphosate which in aqueous solution provides glyphosate anions along with suitable cations or glyphosate acid. Examples of such suitable cations are alkali metal cations, for instance sodium and potassium, and ammonium and substituted ammonium cations. The latter include cations derived from primary or secondary amines such as isopropylamine or dimethylamine, and from diamines such as ethylenediamine. Glyphosate herbicide includes the isopropylamine salts of glyphosate and other agriculturally acceptable salts of glyphosate such as those disclosed in U.S. Pat. No. 3,799,758. Further, examples of agriculturally acceptable salts of glyphosate are trimethyl-sulfonium salt ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the potassium, ammonium and trimethylsulphonium salts as well as the mixed alkylsulfonium salts and trialkylammonium salts.

As used herein, "glufosinate" means N-phosphonomethylalanine in its acid form or any agriculturally acceptable salt of thereof including without limitation the ammonium salt.

In another embodiment of the present invention, the agriculturally active ingredient is a fertilizer. Suitable fertilizers may include, without limitation, inorganic and/or organic fertilizers, fertilizing salts, and mineral fertilizers such as urea, urea phosphate, urea-containing mixed fertilizers, ammonium nitrate, ammonium sulfate-nitrate, ammonium sulfate, mono- and di-ammonium phosphate, monopotassium phosphate, Chilean nitrate, potassium-ammonium phosphate, potassium chloride, potassium nitrate, potassium phosphate, potassium sulfate, sodium nitrate, nitrogenous fertilizers, potassium salts, N, P, K-compound fertilizers, N, P, K-compound fertilizers containing trace elements and combinations of such fertilizers and mineral fertilizers.

Suitable fertilizers may also include chlorides, sulfates, or nitrates of Ca, Mg, Fe, Ni, Mn, Zn, Cu, and Co as well as Mo in the form of water-soluble molybdates and boron in the form of boric acid or boric anhydride. These fertilizers may be in complexed or partially complexed form in order to ensure water solubility. These fertilizers may be complexed with alkali metal salts of N-carboxyalkyl-amino acids. One skilled in the art will recognize other suitable fertilizers for use with this invention.

In other embodiments, the agriculturally active ingredient may include, without limitation: insecticides, fungicides, biocides, molluscicides, algaicides, plant growth regulators, anthelmintics, rodenticides, nematocides, acaricides, amoebicides, protozoacides, crop safeners and combinations thereof. Examples of such agricultural ingredients can be drawn from the Pesticide Dictionary (contained in the Farm Chemicals Handbook) or the British Crop Protection Society: Pesticides Manual, the contents of which are incorporated herein by reference. Agriculturally active ingredients further include chemical substances that are described as "biologically-active ingredients" in International Publication No. WO 2010/009820, which is hereby incorporated by reference. WO 2010/009820 includes, without limitation, descriptions and lists of various pesticides, fungicides, herbicides, insecticides, plant growth regulators, rodenticides, miticides, moluscicides, nematicides and antimicrobials which may be used in embodiments of the present invention. One skilled in the art, with the benefit of this disclosure, will recognize suitable agriculturally active ingredients and combinations thereof for use in this invention.

Embodiments of the present invention include at least one surfactant. The at least one surfactant may include one or more surface active agents capable of reducing the surface tension of water. Surfactants of the present invention may include, without limitation, phosphate esters of akyl ethoxylates and/or alkylaryl ethoxylates; alkylamine ethoxylates and/or etheramine ethoxylates; ethanolamines (such as monoethanolamine (MEA), diethanolamine (DEA), triethanolamine (TEA)) and combinations thereof. Surfactants generally include all surfactants which may show up in the field spray solution or a tank mix. Such surfactants may include, without limitation: aldypolysaccharides, sorbitol and sorbitan esters and ethoxylates of such esters, fatty acid ethoxylates ethoxylated fatty alkanolamines, sulfosuccinates, naphthalene sulfonates, polyoxyethylene polyoxypropylene co-block polymers, alkyl polyoxyethylene polyoxypropylene copolymers, alkyl ethoxylates, aklyaryl ethoxylates, alcohol ether sulfates, alcohol sulfates, alpha olefin sulfonates, salts of dodecylbenzene sulfonic acid, and combinations thereof. One skilled in the art will recognize other suitable surfactants for use in embodiments of the present invention.

Compositions disclosed herein may further comprise other additives. Additives may include but are not limited to utility additives including: humectants, antifoaming agents, dyes and non-surfactant adjuvants such as ammonium sulphate.

Agriculture compositions of the present invention are field ready sprays or tank mixes. Tank mixes are combinations or agricultural products that a consumer, such as a farmer, would pour into a tank, add water and perhaps other adjuvants/additives, mix and then spray/apply on the field. These mixes are typically not stable for extended periods of time, though some of them may have this characteristic. Field ready sprays or tank mixes are distinguishable from stable commercial formulations that have an appreciable stable shelf life and typically need government (for example, FIFRA) registration numbers. Field ready sprays are typically are prepared close to the field to which the material is to be applied. In contrast a commercial pesticide formulation would be formulated at a government approved manufacturing site and in such a concentration that the product must be diluted in water for application.

Embodiments of the present invention further disclose an agricultural adjuvant composition comprising at least one nitrogen containing isethionic acid salt and at least one surfactant. These adjuvants can be used in field ready sprays or tank mixes.

Embodiments of the present invention also disclose a method of treatment of vegetation comprising the step of contacting the agricultural compositions of the present invention to vegetation or soil. Compositions of the present invention may be applied to plants and soils.

Embodiments of the present invention also disclose a method of treatment of a substrate comprising the step of contacting the agricultural compositions of the present invention to the substrate. Such examples may include public health uses of pesticides or animal health formulations. As an example, insecticides may be applied to floors and walls as a preventative treatment. Also, fungicides may be applied to seeds and soils. Compositions of the present invention may be used in other appropriate applications.

The present invention will be further illustrated by a consideration of the following examples, which are intended to be exemplary of the invention.

EXAMPLES

The following adjuvant compositions were produced.

TABLE 1

| Material | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|
| Isethionic Acid 100% | 100 | | 96.5 | 96.4 | 96.3 | 95.7 | 95.5 | 95 | 90 | 85 | 70 |
| SURFONIC ® SI surfactant intermediate | | 100 | | | | | | | | | |
| Ammonium Hydroxide | | | 3.5 | 3.6 | 3.7 | | | | | | |
| Sodium Hydroxide 50% | | | | | | 4.3 | 4.5 | | | | |
| SURFONIC ® T-5 Surfactant | | | | | | | | 5 | 10 | 15 | 30 |

Examples 1-11 Compared with Control Example

Isethionic acid (Example 1) and ten neutralization products of isethionic acid (Examples 2-11) were used to treat aqueous spray tank solutions of isopropylamine glyphosate in order to measure the water conditioning efficacy of isethionic acid and the other isethionates. Isethionic acid was neutralized with sodium (Examples 2, 6, and 7), ammonia (Examples 3-5) and tallow amine ethoxylates (Examples 8-11—SURFONIC® T-5 surfactant). These candidates were evaluated against the standard agricultural water conditioner, ammonium sulfate in an aqueous tank mix of isopropylamine glyphosate (Control Example). Specifically, the candidates were tested for their ability to condition water as a function of the suppression of water hardness inhibition of pesticides, such as glyphosate. All evaluations were run in the absence of any surfactant in standard hard water as defined by the World Health Organization standard hard waters. The evaluations were run in greenhouse conditions over a variety of plant species, including determining injury to crop species. The reported data was percent control of target weed species and percent injury to crop species. All evaluations (except for one industry standard) were conducted in the absence of any surfactant.

The surprising result in these determinations was that the isethionic acid and its neutralants functioned at a level comparable to that of the agricultural industry standard ammonium sulfate.

Examples 12 and 13 show embodiments of agricultural adjuvant compositions. Two compositions were produced and are shown in Table 2. The surfactants used are SURFONIC® N-95 surfactant and TERWET® 3001 adjuvant. SURFONIC® N-95 surfactant is a nonylphenol ethoxylate. TERWET® 3001 is a $C_{8-10}$ alkyl polyglucoside. Both surfactants are commercially available from Huntsman Corporation of The Woodlands, Tex.

TABLE 2

| Ingredients | Example 12 | Example 13 |
|---|---|---|
| SURFACTANT | | |
| SURFONIC ® N-95 SURFACTANT | 60.0 | |
| TERWET ® 3001 ADJUVANT | | 15.0 |
| NH$_4$ISETHIONATE | 20.0 | 58.0 |
| WATER (DEIONIZED) | 20.0 | 2.0 |
| GLYCERINE | | 25.0 |
| | 100.0 | 100.0 |
| Results: | CLEAR | CLEAR |

Examples 12 and 13 show that clear, homogeneous formulations can be made with ammonium isethionate.

Although the present invention and its advantages have been described in detail, it should be understood that various changes, substitutions and alterations may be made herein without departing from the spirit and scope of the invention as defined by the appended claims.

What is claimed is:

1. An agricultural composition comprising:
   a) at least one nitrogen containing isethionic acid salt,
   b) at least one weak acid agriculturally active ingredient, and
   c) at least one surfactant,
   wherein the agricultural composition is a field ready spray or a tank mix, wherein the at least one nitrogen containing isethionic acid salt comprises tallow amine isethionic acid salt.

2. An agricultural composition comprising:
   a) at least one nitrogen containing isethionic acid salt,
   b) at least one weak acid agriculturally active ingredient, and
   c) at least one surfactant,
   wherein the agricultural composition is a field ready spray or a tank mix, wherein the at least one weak acid agriculturally active ingredient comprises n-phosphonomethylglycine.

3. A composition according to claim 1, wherein the at least one weak acid agriculturally active ingredient is selected from the group consisting of: an insecticide, a fungicide, a biocide, a molluscicide, an algaicide, a plant growth regulator, an anthelmintic, a rodenticide, a nematocide, an acaricide, an amoebicide, a protozoacide, a crop safener and a combination thereof.

4. A composition according to claim 1 wherein the at least one surfactant comprises one or more surface active agents capable of reducing the surface tension of water.

5. The agricultural composition of claim 1, wherein the at least one nitrogen containing isethionic acid salt further comprises ammonium isethionic acid salt.

6. The agricultural composition of claim 2, wherein the at least one nitrogen containing isethionic acid salt comprises ammonium isethionic acid salt.

7. The agricultural composition of claim 2, wherein the at least one surfactant comprises one or more surface active agents capable of reducing the surface tension of water.

8. The agricultural composition of claim 5, wherein the at least one surfactant comprises one or more surface active agents capable of reducing the surface tension of water.

9. The agricultural composition of claim 6, wherein the at least one surfactant comprises one or more surface active agents capable of reducing the surface tension of water.

* * * * *